(12) United States Patent
Woodson

(10) Patent No.: US 12,091,396 B1
(45) Date of Patent: Sep. 17, 2024

(54) SYSTEM AND METHOD FOR REACTING ONE OR MORE COMPOUNDS TO FORM TETRAHYDROCANNABINOLIC ACID (THCA)

(71) Applicant: Adam Woodson, Damascus, VA (US)

(72) Inventor: Adam Woodson, Damascus, VA (US)

( * ) Notice: Subject to any disclaimer, the term of this patent is extended or adjusted under 35 U.S.C. 154(b) by 0 days.

(21) Appl. No.: 17/496,568

(22) Filed: Oct. 7, 2021

(51) Int. Cl.
*C07D 311/78* (2006.01)
*C07D 311/80* (2006.01)

(52) U.S. Cl.
CPC .................................. *C07D 311/78* (2013.01)

(58) Field of Classification Search
CPC .............................. C07D 311/78; C07D 311/80
See application file for complete search history.

(56) References Cited

FOREIGN PATENT DOCUMENTS

WO  WO-2021062557 A1 * 4/2021 ........... C07D 311/80

OTHER PUBLICATIONS

Gulzar, A., A. Gulzar, M. Ansari, F. He, S. Gai and P. Yang, "Carbon dioxide utilization: A paradigm shift with CO 2 economy", Chemical Engineering Journal Advances 3 (2020), 100013, pp. 1-25. (Year: 2020).*

* cited by examiner

*Primary Examiner* — Amanda L. Aguirre
*Assistant Examiner* — Sagar Patel
(74) *Attorney, Agent, or Firm* — Leavitt Eldredge Law firm; Richard G Eldredge

(57) ABSTRACT

A method of producing tetrahydrocannabinolic acid (THCA), the method includes obtaining a starting compound, the starting compound being selected from the group consisting of delta 9-THC, delta 8-THC, and delta 10-THC; placing the starting compound into a high pressure reaction chamber; treating the starting compound with a high heat, a high pressure, and carbon dioxide within the high pressure reaction chamber to create a resulting product; and treating the resulting product with sulfuric acid to yield the THCA.

1 Claim, 2 Drawing Sheets

SYSTEM AND METHOD FOR REACTING ONE OR MORE COMPOUNDS TO FORM TETRAHYDROCANNABINOLIC ACID (THCA)

BACKGROUND

1. Field of the Invention

The present invention relates generally to chemical reaction systems, and more specifically, to a system and method that utilizes one or more chemical reactions to form tetrahydrocannabinolic acid (THCA).

2. Description of Related Art

Chemical reaction systems are well known in the art and are effective means to form various compounds. In the *cannabis* industry, there is currently a rise in the desire to produce the cannabinoid THCA for its potential therapeutic effects. For example, research has demonstrated that THCA offers similar benefits to the more common tetrahydrocannabinol (THC) but without some of the potentially negative effects for some users, such as an associated psychoactive effects.

Accordingly, there is a desire and need to achieve methods of forming THCA effectively and efficiently.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
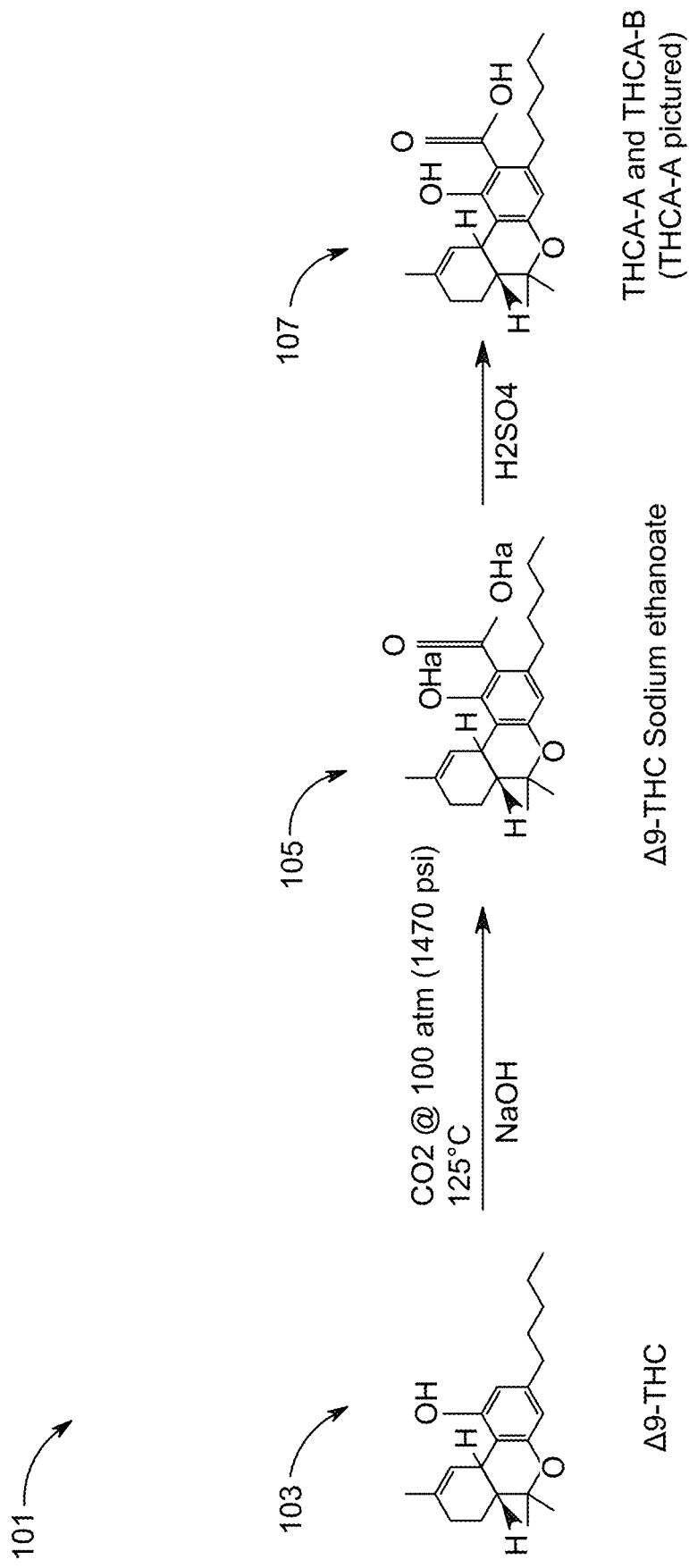
FIG. 1 is a chemical reaction depiction according to the preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional chemical reaction systems. Specifically, the present invention provides a means to produce THCA in an effective and efficient manner. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a chemical reaction 101 in accordance with a preferred embodiment of the present application. It will be appreciated that reaction 101 produces THCA as the objective of the present invention. In some embodiments, it should be appreciated that the ending product is CBDA as will be discussed herein.

As shown, the reaction 101 begins with a starting compound 103 which in the example shown is delta delta 9-THC, however it should be appreciated that other compounds such as delta 8-THC, or delta 10-THC could be used. Further, the starting compound may be CBD. This compound is added to a high pressure chamber for a chemical reaction, wherein the compound undergoes carboxylation reaction by being heated to approximately 125 degrees Celsius and treated with carbon dioxide under high pressure at approximately 1470 psi. The resulting product 105 is treated with sulfuric acid to yield the end product, namely THCA 107 in the example shown. In alternative examples, CBDA is the ending product. This carboxylation reaction is commonly known as the Kolbe reaction mechanism.

Figure 2:
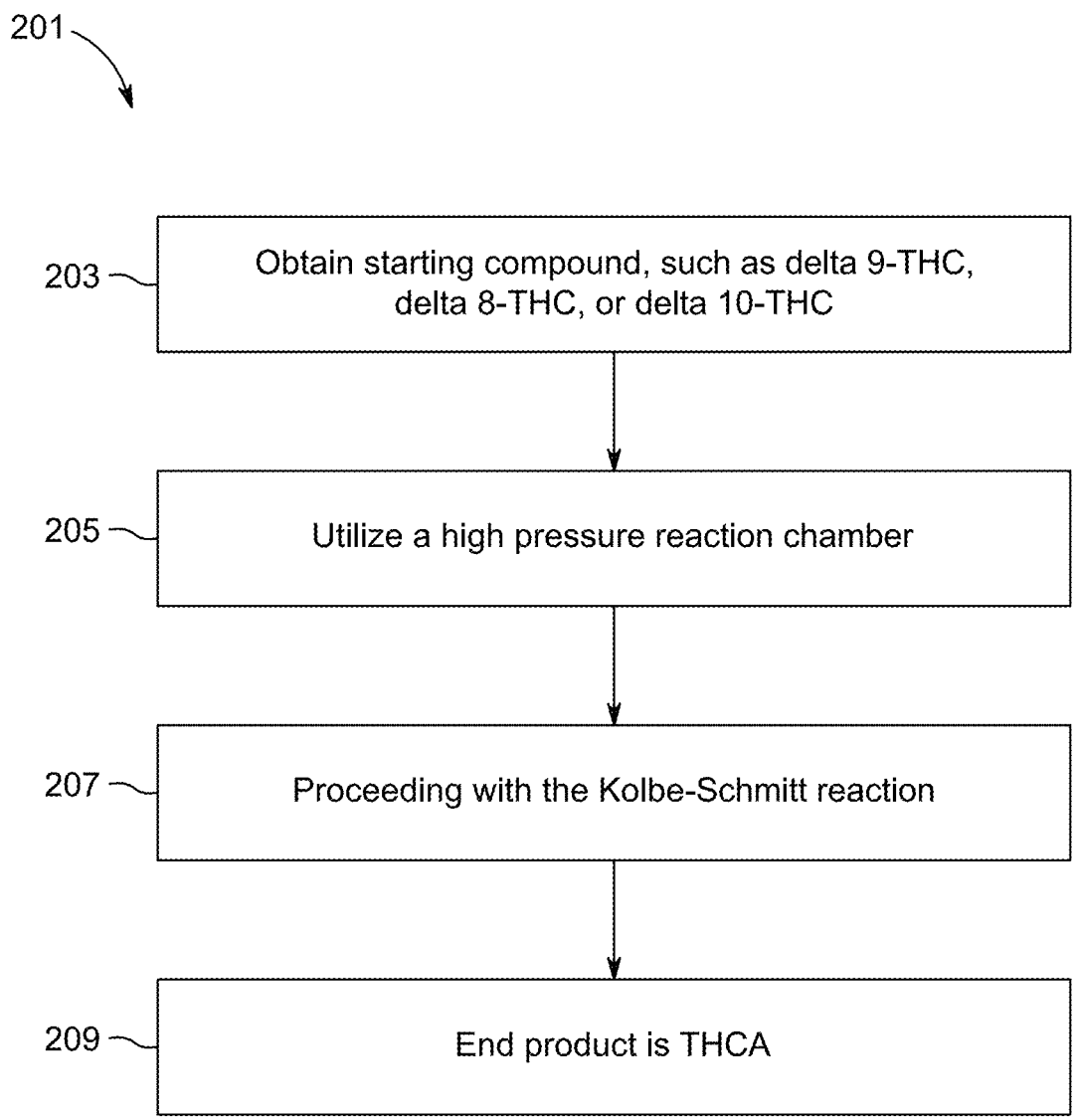
FIG. 2 is a flowchart depicting the method in accordance with the present application.

In FIG. 2, a flowchart 201 further depicts the process discussed above. As shown, the beginning compound is selected, as shown with box 203. The compound is then added to the high pressure reaction chamber, wherein the Kolbe-Schmitt reaction discussed above is utilized to produce THCA or CBDA, as shown with boxes 205, 207, 209.

It should be appreciated that one of the unique features believed characteristic of the present application is the production of THCA or CBDA using the Kolbe Schmitt reaction. It should be appreciated that this process will produce color free THCA which will be ideal for the end consumer. Further, it should be appreciated that this process results in no loss of THC or THCA due to color remediation filter medias. Lastly, it is contemplated and should be appreciated that the system and method discussed herein could be used for CBD to CBDA and possibly the conversion of CBN to THC.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A method of producing tetrahydrocannabinolic acid (THCA), the method comprising:
    obtaining a starting compound, the starting compound being selected from the group consisting of delta 9-THC, delta 8-THC, and delta 10-THC;
    placing the starting compound into a high pressure reaction chamber;
    treating the starting compound with carbon dioxide within the high pressure reaction chamber at a temperature of 125 degrees Celsius and at a high pressure of 1470 psi to create a 9-THC sodium ethanoate compound; and
    treating the 9-THC sodium ethanoate compound with sulfuric acid to yield the THCA.

* * * * *